United States Patent [19]
Carlisle et al.

[11] Patent Number: 5,480,430
[45] Date of Patent: Jan. 2, 1996

[54] SHAPE-RETAINING SHELL FOR A FLUID FILLED PROSTHESIS

[75] Inventors: Daniel A. Carlisle, Santa Barbara, Calif.; G. Patrick Maxwell, Nashville, Tenn.

[73] Assignee: McGhan Medical Corporation, Santa Barbara, Calif.

[21] Appl. No.: 320,121

[22] Filed: Oct. 7, 1994

Related U.S. Application Data

[63] Continuation of Ser. No. 73,682, Jun. 4, 1993, abandoned.
[51] Int. Cl.⁶ .............................. A61F 2/12; A61F 2/52; A61F 2/02
[52] U.S. Cl. ........................... 623/8; 623/7; 623/11
[58] Field of Search .................. 623/7, 8, 11, 17; 206/524.6

[56] References Cited

U.S. PATENT DOCUMENTS

| | | | |
|---|---|---|---|
| 4,217,889 | 8/1980 | Radovan et al. | 623/8 |
| 4,332,634 | 6/1982 | Aperavich | 623/8 |
| 4,795,464 | 1/1989 | Ebert et al. | 623/8 |
| 4,840,615 | 6/1989 | Hancock et al. | 623/8 |
| 4,899,764 | 2/1990 | Gauger et al. | 623/8 |

*Primary Examiner*—Debra S. Brittingham
*Attorney, Agent, or Firm*—Michael G. Petit

[57] ABSTRACT

A fluid-filled breast prosthesis for surgical implantation beneath the skin having a wrinkle resistent, elastic outer shell which is adapted to resist deformation or wrinkling during movement of the fluid filler. The outer shell, or envelope, has superior and inferior portions. The wall of the superior portion of the shell is substantially thickened with respect to the wall thickness of the inferior portion of the shell. The shell forms an envelope with an inner cavity which is filled with a biocompatible liquid such as saline. The presence of the thickened superior portion of the shell prevents wrinkles from forming in the breast prosthesis during fluid displacement such as occurs when the breast prosthesis recipient changes her anatomical position. The differentially thickened shell has a posterior base portion which may be reinforced to further stabilize the prosthesis.

4 Claims, 1 Drawing Sheet

SHAPE-RETAINING SHELL FOR A FLUID FILLED PROSTHESIS

CROSS REFERENCE TO RELATED APPLICATIONS

This is a continuation of application Ser. No. 08/073,682; filed Jun. 4, 1993, now abandoned.

BACKGROUND OF THE INVENTION

1. Field of the Invention

The present invention relates generally to fluid-filled prostheses and more particularly to a fluid-filled breast prosthesis which can be implanted beneath the skin to replace or augment the female breast.

2. Prior Art

In the field of plastic surgery, it has become a frequent practice to implant a prosthesis in the area of the female breast for reconstruction or augmentation. In the case of reconstruction, cancerous, pre-cancerous or other abnormal or damaged tissue has been removed. This creates a void where the tissue has been removed. A prosthesis may then be inserted through the incision to fill this void. The prosthesis then becomes a permanent replacement for the damaged tissue which has been removed, and its purpose is to restore the body contour to its original configuration. The prosthesis then furnishes support for the surrounding body tissue and organs to preserve as closely as possible the original appearance of the body.

Clinical problems have become apparent with permanent fluid-filled implantable prosthesis. Rippling, knuckling and airage palpation are major problems. Since saline, lacking the visco-elastic properties and memory of silicone gel, transmits fluid waves; ripples, knuckles, and fluid waves are more easily transmitted to the overlying skin. Silicone gel solves many of these problems because its visco elasticity prevents fluid waves.

The problems with saline-filled breast implants are well known in the art. The primary difficulty with such breast implants is that they don't feel like breast tissue. That is, the saline filler is less viscous than breast tissue and sloshes about within the implant giving it a quite unnatural feel. Another related problem is the wrinkling that occurs in the superior portion of a breast implant when the stretchable elastomer outer shell is weighted down by the saline.

Various fillers have been proposed to partially mitigate these problems. Pangman, in U.S. Pat. No. 3,366,975, suggested the use of a plastic form core to fill the breast prosthesis. Pangman's prosthesis comprised a core of plastic foam surrounded by a membrane which is impervious to fluids. The impervious membrane is, in turn, covered by a porous layer to which human tissue can adhere. The core in the Pangman prosthesis prevents wrinkling and is shaped to restore the body to its initial shape and appearance following breast removal. Many of the suggestions of Pangman regarding prostheses design are now incorporated commonly in breast prosthesis. Certainly, the textured outer surface suggested by Pangman to promote tissue ingrowth is a common feature in the outer shell of today's prosthesis. The sponge or foam core has not been widely used for various reasons. One of the reasons is that it is difficult to synthesize a foam which truly mimics human tissue.

Since currently a certain number of patients will not or cannot accept silicone gel implants and desire saline, a shell is needed which will minimize the problems eluded to above. Shells having a cover portion and a reinforced base portion are well in the art. Radovan et al., in U.S. Pat. No. 4,217,889, disclose a shell having a non-extensible base. This base comprises silicone with a fabric or even a metal plate embedded therein to create a stiff, slightly flexible base portion. According to Radovan et al. (Col. 5, lines 40–44), "The cover is preferably relatively thin, on the order of approximately 2020 inch thick, while the base is relatively thicker and reinforced, preferably on the order of about 0.04 inch, with a polyester fabric reinforced embedded therein." Radovan et al. also teach that the difference in extensibility between the cover and the base can be provided by differences in the thickness of the material; the base being thicker than the cover. Thus, while Radovan et al. show the advantage to be gained by reinforcing the base of a tissue expander as, for example, by thickening the base relative to the cover, they do not teach an advantage to reinforcing the cover of the shell (or portions thereof) as, for example, by thickening. Most frequently, shell deformation occurs in the superior (upper) portion of a breast implant. It is desirable to provide a fluid-filled implant which has the safety inherent in water or saline-filled implants, but without the disadvantage of wrinkling or deformation that occurs with prior art saline-filled implants when the wearer changes position.

SUMMARY OF THE INVENTION

It is an object of this invention to provide an outer shell for a fluid-filled implant which resists deformation or wrinkling regardless of the position of the patient.

It is another object of this invention to provide a breast prosthesis which is easily positioned within the human body and which simulates the physical and mechanical behavior of breast tissue in various positions of the host.

These and other objects of the invention will now become apparent as we turn to the preferred embodiment.

DESCRIPTION OF THE PREFERRED EMBODIMENT

Figure 1:
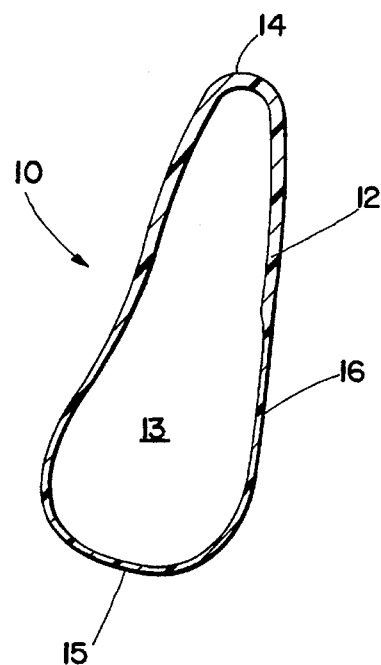
FIG. 1 is a cross sectional side view of a breast prosthesis made according to the present invention.
Figure 2:
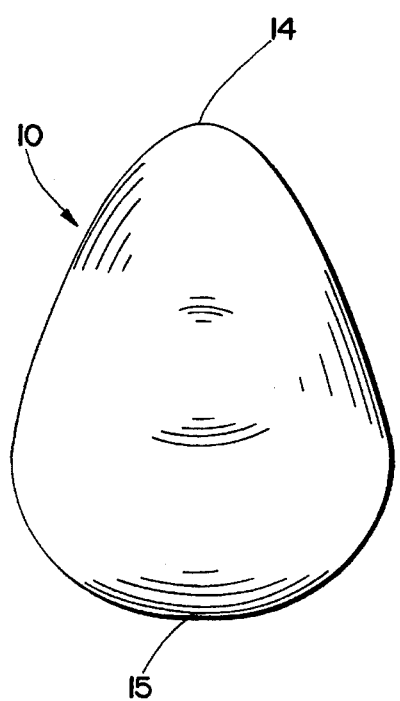
FIG. 2 is an anterior view of the preferred embodiment of the present invention shown in FIG. 1.

Turning now to FIG. 1, a preferred embodiment of the prosthesis of the present invention is generally indicated at the numeral 10. The prosthesis comprises an elastomeric shell 11, typically made of a bio-compatible elastomer such as silicone which may conveniently be made by dip casting over a mandril dimensioned to approximate the shape of the prosthesis. The shell can, of course, also be molded to the proper shape and wall thickness. The outer shell 11 has a variable wall thickness; being substantially thicker at the superior portion 14 forming the upper half of the shell 11 than at the inferior portion 15 which inferior portion forms the lower half of the shell 11. Preferably, the wall thickness of the superior portion 14 of the shell 11 is at least twice as thick as the wall thickness of the inferior portion 15 of the shell 11. The elastomer 12 comprising the wall of the superior aspect 14 of the shell 11 is preferably cured silicone, although it may be a silicone foam, either open or closed cell, or it may be a vulcanized silicone rubber of a relatively low durometer. The material for the shell, which may be a composite, should be chosen to prevent loss of the filler material from the cavity 13 as, for example, by bleeding or diffusion. The interior of the shell 11 describes a cavity indicated at 13. The cavity 13 may be filled with either normal saline, water or any other biocompatible filling material. The posterior portion of the shell 11 comprises the base 16 of the prosthesis. The inferior portion of the base 16 may also be thickened or otherwise reinforced to facilitate implantation of the prosthesis or to stabilize the prosthesis after implantation.

Figure 3:
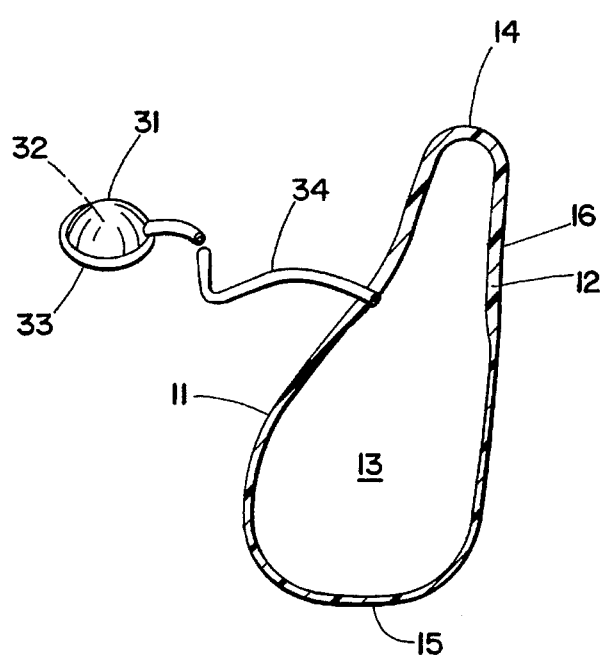
FIG. 3 is a cross-sectional side view of the breast prosthesis of FIG. 1 with a remote filler tube attached thereto.

The prosthesis 10 can be filled at the time of surgery or only partially filled prior to insertion into the patient. This can be accomplished by direct fluid injection through a self sealing valve (not shown) in an integral injection port (not shown) or a remote injection port as shown in FIG. 3. The remote injection port, generally indicated at 31, has an outer self-sealing septum, which is self sealing to the track of a needle which encloses an injection reservoir 32. A puncture-proof backing 33 completes the enclosure of the reservoir. A channel 34 provides fluid communication between the injection reservoir 32 and the interior cavity 13 of the breast prosthesis 10. After implantation, the volume of the prosthesis may be adjusted by placing a needle through the skin to pierce the septum 31 and enter the injection reservoir 32. Any air which may be present in the prosthesis is then aspirated and a suitable fluid is injected to replace the removed air. Alternatively, an integral fill port (not shown) of a type well known in the art (see, for example, U.S. Pat. No. 4,671,255 to Dubrul) can be used to fill the prosthesis either before, during or after implantation.

If a remote injection port is used, as shown in FIG. 3, after the size of the prosthesis has been adjusted as required, the entire fill port 31 and fill tube 34 may be removed. It is customary in this regard to have the fill tube 34 entering the shell through a self-sealing valve (not shown) which seals when the fill tube is removed. Such valves that are self-sealing to the removal of a fill tube are well known in the art (see, for example, U.S. Pat. No. 4,930,535 to Rinehold).

Thus, we have described a new type of fluid-filled implantable breast prosthesis which prevents wrinkling or other significant deformation regardless of the position of the recipient of the implant. This is accomplished by thickening the superior portion of the shell of the prosthesis 10. Following implantation, the superior portion of the implant is anchored to surrounding tissue. The wrinkling, when it occurs, normally occurs at the superior aspect of the prosthesis when the weight of the saline or filler in the cavity 13 stretches the elastomeric shell 11 as, for example, when the patient is standing. Thickening the wall of the superior aspect of the shell to prevent wrinkling significantly improves the appearance of such a prosthesis.

Although the invention has been described with respect to certain of its more important features, it will be understood that the invention is subject to variations and modifications without departing from its broader scope. Thus, for example, the outer shell may be either textured, differentially textured, or not textured. The superior portion of the prosthesis is preferably silicone, but may be any biocompatible elastomeric material. Thus, a silicone foam, either open or closed cell, may be an acceptable material for thickening the superior aspect of the shell as would any other elastomeric biocompatible material having tissue-like characteristics. The posterior portion of the shell may be thickened or otherwise reinforced to facilitate implantation and/or stabilize the prosthesis following implantation. In addition to being useful as a mammary prosthesis, the improved implantable prosthesis of this invention can also be used for different shapes and forms for the purpose of augmenting tissue anywhere on the animal or human body for aesthetic and reconstructive purposes. As far as the fluid filler goes, while normal saline or sterile water are currently preferred fillers, any other bio-compatible and acceptable filler such as hyaluronic acid, hydrogel solutions or dextran might be equally acceptable as a liquid filler. Accordingly, it is to be understood that the foregoing description is considered as being illustrative of, rather than limitative upon, the invention as defined by the appended claims.

What I claim is:

1. A fluid-filled prosthesis adapted for permanent implantation beneath the skin of a person comprising an outer shell of varying wall thicknesses, said outer shell having the general shape of a breast, said shell being divided into superior and inferior halves wherein a substantial portion of the superior half having a first wall thickness and the inferior half having a second wall thickness, said first wall thickness being greater than said second wall thickness and wherein said superior portion is that half of the prosthesis which is uppermost when the prosthesis is implanted beneath the skin of the person and the person is erect.

2. The fluid filled breast prosthesis of claim 1 wherein said first wall thickness is at least twice as great as said second wall thickness.

3. The fluid-filled breast prosthesis of claim 1 further comprising a means for transdermally adjusting the volume of fluid in said fluid-filled prosthesis following implantation.

4. The fluid-filled breast prosthesis of claim 2 further comprising a means for transdermally adjusting the volume of fluid in said fluid-filled prosthesis following implantation.

* * * * *